(12) United States Patent
Gravesen et al.

(10) Patent No.: US 7,431,052 B2
(45) Date of Patent: Oct. 7, 2008

(54) FLOW RESTRICTOR AND SYSTEM FOR DELIVERING A FLOW OF LIQUID IN A MICROCAPILLARY

(75) Inventors: Peter Gravesen, Nordborg (DK); Martin Manscher, Valby (DK); Per Brandt Rasmussen, Augustenborg (DK)

(73) Assignee: Danfoss A/S, Nordborg (DK)

( * ) Notice: Subject to any disclaimer, the term of this patent is extended or adjusted under 35 U.S.C. 154(b) by 207 days.

(21) Appl. No.: 10/570,979

(22) PCT Filed: Sep. 4, 2004

(86) PCT No.: PCT/DK2004/000587

§ 371 (c)(1),
(2), (4) Date: May 15, 2006

(87) PCT Pub. No.: WO2005/023339

PCT Pub. Date: Mar. 17, 2005

(65) Prior Publication Data

US 2007/0012371 A1    Jan. 18, 2007

(30) Foreign Application Priority Data

Sep. 10, 2003    (DK) ............................... 2003 01301

(51) Int. Cl.
F16L 55/00    (2006.01)

(52) U.S. Cl. ................... 138/40; 251/118; 604/246

(58) Field of Classification Search ........... 251/118, 251/120, 121; 138/40, 44, 45, 46; 604/246, 604/250, 67

See application file for complete search history.

(56) References Cited

U.S. PATENT DOCUMENTS 3,898,637 A    8/1975  Wolstenholme .......... 340/239

(Continued)

FOREIGN PATENT DOCUMENTS

EP    0 737 483 A1    10/1996
WO    96/23534    8/1996

OTHER PUBLICATIONS

Article entitled "The clogging pressure of large bubbles in microchannel contractions" by M. Jensen et al., Mikroelektronik Centret (MIC), Technical University of Denmark, Jun. 7, 2003, pp. 1-22.
Article entitled "Quasi-static Motion of Bubbles in Microchannel Contractions" by M. Jensen et al., Mikroelektronik Centret (MIC), Technical University of Denmark, undated, pp. 1-4.

(Continued)

*Primary Examiner*—John Bastianelli
(74) *Attorney, Agent, or Firm*—McCormick, Paulding & Huber LLP

(57) ABSTRACT

The present invention relates to apparatus for delivering a controlled or restricted flow of liquid and limiting bubble fragmentation at the inlet. This is achieved in flow restrictor with a flow channel having over most of its length a substantially constant, minimum hydraulic diameter $D=4A/W$ wherein A is the minimum local cross-sectional area of the channel and W is the minimum local wetting perimeter of the channel, by smoothly widening the channel at its inlet such that:

at distances z from the inlet face with $0<z<z_1$, the channel has a hydraulic diameter $D_z \geq k*D$ wherein $k \geq 1.3$;

at distances z from the inlet face with $z_1 < z < z_2$, the channel has a hydraulic diameter $D_z$ with $k*D \geq D_z \geq D$; and at distances z from the inlet face with $z_2 < z$, the channel has a hydraulic diameter $D_z$ with $D_z \leq 1.02D$, except possibly for a similar widening of the channel at the outlet. It has been found that widening the flow channel at the inlet, such that its diameter increases smoothly and gradually, and preferably by a factor of at least 1.3 over a length of at least 3 channel diameters, significantly reduces the tendency towards bubble fragmentation in microcapillary flow restrictors, and also substantially increases the yield of devices which operate well.

3 Claims, 1 Drawing Sheet

U.S. PATENT DOCUMENTS

| | | | |
|---|---|---|---|
| 4,037,596 A | | 7/1977 | LeFevre et al. .............. 128/214 |
| 4,192,303 A | * | 3/1980 | Young et al. ................... 138/46 |
| 4,312,010 A | | 1/1982 | Doring ................... 346/140 R |
| 4,934,375 A | * | 6/1990 | Cole et al. .................. 604/246 |
| 5,085,058 A | | 2/1992 | Aaron et al. ............... 62/324.6 |
| 5,489,265 A | | 2/1996 | Montalvo et al. .............. 604/67 |
| 6,102,897 A | * | 8/2000 | Lang .......................... 604/246 |

OTHER PUBLICATIONS

Article entitled "A capillary suction probe for bubble size measurement" by M. Barigou et al., Measurement Science & Technology, Apr. 2, 1991, No. 4, Bristol, GB, pp. 318-326.

* cited by examiner

FLOW RESTRICTOR AND SYSTEM FOR DELIVERING A FLOW OF LIQUID IN A MICROCAPILLARY

CROSS REFERENCE TO RELATED APPLICATIONS

This application is entitled to the benefit of and incorporates by reference essential subject matter disclosed in International Patent Application No. PCT/DK2004/000587 filed on Sep. 4, 2004 and Danish Patent Application No. PA 2003 01301 filed Sep. 10, 2003.

FIELD OF THE INVENTION

The present invention relates to apparatus for delivering a controlled or restricted flow of liquid. An example of such apparatus is an infusion pump for delivering a controlled flow of medication to a patient during a certain period of time which can be a number of days. Other applications might be envisaged in the chemical or biotechnology fields.

BACKGROUND OF THE INVENTION

In medical infusion, the flow typically needs to be restricted to rather low rates, such as, for example, 1000 microlitres per hour. Delivery of liquids at flow rates of a few millilitres per hour or less may be realized by connecting a source of pressurized liquid to a capillary of small internal diameter. In capillaries the rate of flow through the capillary has a well-defined relation to the length and diameter of the capillary, and to the difference in pressure between the capillary inlet and the capillary outlet. For any given pressure difference the flow rate may thus be fixed at a desired value by choosing a capillary of suitable length and diameter.

A problem with capillaries of very small internal diameter (microcapillaries) is that bubbles of gas in the liquid may have a serious impact on the pressure difference or pressure drop required to drive a given flow rate through the capillary, and in the worst case bubbles may lead to an effective blocking of the capillary. This is due to the phenomenon of fragmentation of a (larger) bubble at the inlet of the capillary into a plurality of small bubbles within the capillary. The small bubbles are separated from each other by plugs of liquid, and each small bubble requires a certain pressure difference between its ends to move along the capillary. That pressure difference is largely independent of bubble length. Bubble fragmentation at the inlet may fill the capillary with so many small bubbles that the pressure difference available for generating liquid flow is reduced or fully consumed by the sum of pressure drops needed to drive the small bubbles along the capillary. Therefore, flow through the capillary may be severely reduced or even stopped by bubble fragmentation.

Fused silica microcapillaries with an internal diameter of 10 to 100 micrometers are widely used in the field of chemical analysis, in applications such as capillary electrophoresis and gas chromatography. Microcapillary flow restrictors for use in medical infusion are easily made by cutting suitable lengths (a few centimeters each) off from fused silica microcapillary stock. Other choices of material are also available, such as polymeric capillaries or micromachined planar capillary structures.

Unfortunately, however, experience shows that the occurrence of bubble fragmentation in microcapillary flow restrictors is not predictable. Out of 100 flow restrictors made, some may have a very low tendency towards bubble fragmentation whereas others will fragment virtually any bubble that enters. There is a lack of yield and a lack of predictability. Both are major obstacles in the industrial use of microcapillary flow restrictors, for example in mass fabrication of medical infusion devices.

BRIEF SUMMARY OF THE INVENTION

It is an object of the present invention to devise a flow restrictor structure which has less tendency towards bubble fragmentation, which is more predictable in its bubble fragmentation behaviour and which provides a higher yield of usable devices than commonly known microcapillary flow restrictors.

This is achieved in flow restrictor with a flow channel having over most of its length a substantially constant, minimum hydraulic diameter $D=4A/W$ wherein A is the minimum local cross-sectional area of the channel and W is the minimum local wetting perimeter of the channel, by smoothly widening the channel at its inlet such that:

at distances z from the inlet face with $0<z<z_1$, the channel has a hydraulic diameter $D_z \geq k*D$ wherein $k \geq 1.3$;

at distances z from the inlet face with $z_1<z<z_2$, the channel has a hydraulic diameter $D_z$ with $k*D \geq D_z \geq D$; and at distances z from the inlet face with $z_2<z$, the channel has a hydraulic diameter $D_z$ with $D_z \leq 1.02D$, except possibly for a similar widening of the channel at the outlet.

It has been found that widening the flow channel at the inlet, such that its diameter increases smoothly and gradually, and preferably by a factor of at least 1.3 over a length of at least 3 channel diameters, significantly reduces the tendency towards bubble fragmentation in microcapillary flow restrictors, and also substantially increases the yield of devices which operate well.

BRIEF DESCRIPTION OF THE DRAWINGS

A preferred embodiment of the invention will now be described in detail with reference to the drawings.

DETAILED DESCRIPTION OF THE INVENTION

Figure 1:
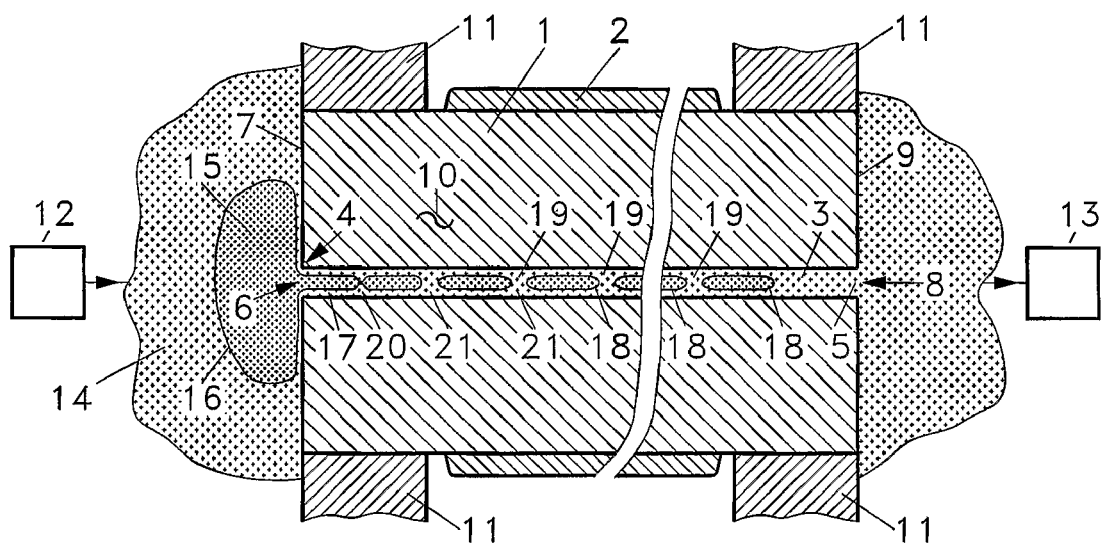
FIG. 1 is a flow restrictor made by cutting a length off from microcapillary stock; and in FIG. 2 is a flow restrictor made by gradually widening the internal diameter of a microcapillary at the inlet, in accordance with the invention.

FIG. 1 shows a capillary flow restrictor 10 made by cutting off a length of microcapillary which is commercially available from various vendors for use in the field of chemical analysis (gas chromatography, capillary electrophoresis etc).

The device 10 is an elongated tube whose wall 1 is made from fused silica (quartz glass) with an outer cladding 2 of polyimide. The wall 1 surrounds a flow channel 3 of circular or rectangular (for example, square) cross-section which extends from an inlet 4 to an outlet 5. At the inlet, the flow channel 3 forms an inlet opening 6 in an inlet face 7 of the flow restrictor, and at the outlet it forms an outlet opening 8 in an outlet face 9 of the flow restrictor. Depending on how the device was cut off, the inlet face 7 and the outlet face 9 of the device may be smooth (from abrasive cutting) as shown at 7 or slightly rough (from scoring and breaking) as shown at 9.

The flow restrictor 10 is mounted in a flow system for delivering a controlled flow of liquid from a source 12 of liquid 14 to a recipient 13. The source 12 is pressurized in a suitable way, not shown, to a pressure which his higher than the pressure prevailing at the recipient 13. For example, in a medical infusion system the source 12 may be an inflated bladder at a pressure of about 300-2000 mbar above recipient pressure, and the recipient 13 may be a blood vessel or any other suitable internal location in the body of a patient who has received the entire flow system as an implant.

Mounting detail is schematically indicated at both ends of the flow restrictor, where the polyimide cladding has been removed to allow direct contact between a fluid-tight clamping system, indicated as 11, and the body 1 of the capillary tube.

The liquid 14 may contain bubbles of gas 15. One such bubble 16 is shown as being driven into the inlet 4 of the flow channel 3 by the pressure difference between source and recipient. Often the presence of the bubble causes two-phase flow at the channel inlet 4. Liquid flows in a thin layer 17 which adheres to the inner surface of the channel 3. The liquid layer 17 coaxially surrounds a flow 18 of gas which fills the remaining core of the channel 3.

The two-phase flow in the flow channel 3 exhibits a phenomenon of instability, which frequently leads to fragmentation of the gas flow into separate bubbles 18 of gas separated by plugs 19 of liquid. This is due to the surface tension of the liquid-gas interface of the film 17. The surface tension causes a tendency of the liquid film to reduce its surface. Perturbations having a wavelength longer than $\pi \ast D$ (where D is the hydraulic diameter of the channel as defined earlier) may grow until a bubble is pinched off as indicated at 20 and 21. Such fragmentation is frequently observed, although its onset has turned out in practice to be largely unpredictable. It leads to the generation of a plurality of small bubbles each having a length $L_{min}$ of the order of the wetted perimeter of the channel, $\pi \ast D$.

As is commonly known, the flow of liquid through the channel 3 follows the law of Hagen-Poiseuille:

$$Q = \frac{\partial D^4 \Delta P}{128 \varsigma_1 L} \quad (1)$$

wherein Q is the flow rate, D is the hydraulic diameter of the flow channel, $\Delta P$ is the pressure difference between the inlet and the outlet of the flow channel, L is the length of the flow channel and $\eta_l$ is the viscosity of the liquid. Rearranging equation (1) we get $$\Delta P = \frac{128 Q \varsigma_1 L}{\partial D^4} \quad (2)$$

as an expression indicating the pressure drop required to drive the flow rate Q of liquid through the channel 3.

In the case of a flow of gas through the channel 3, the same expression (2) would apply with the viscosity $\eta_g$ of the gas substituted for the viscosity $\eta_l$ of the liquid.

In the case of bubble fragmentation it is known that each gas bubble requires a deformation pressure drop $$\Delta P_d = \frac{4\acute{a}}{D} \quad (3)$$

to move along the channel 3, which is caused by the fact that the front and rear surface of a bubble take on different shapes during movement of the bubble. In equation (3), α is a frictional surface tension parameter which must be established empirically, and D is the hydraulic diameter of the channel. Thus, the pressure drop $\Delta P_b$ required to drive a bubble along the channel 3 will be the sum of the viscous and deformation pressure drops:

$$\Delta P_b = \frac{4\acute{a}}{D} + \frac{128 Q \varsigma_g L_b}{\partial D^4} \quad (4)$$

wherein $L_b$ is the length of channel taken up by the bubble. On the other hand, because a gas bubble replaces a plug of liquid of the same length and the viscosity of gas is generally lower than the viscosity of liquid, a gas bubble may flow more easily through the channel 3 than a plug of liquid of the same length. Combining equations (2) and (4), the replacement a plug of liquid with a gas bubble leads to no change in the pressure drop if:

$$\Delta(\Delta P) = -\frac{128 Q \varsigma_1 L_b}{\partial D^4} + \frac{128 Q \varsigma_g L_b}{\partial D^4} + \frac{4\acute{a}}{D} = 0 \quad (5)$$

wherein $L_b$ is again the length of the bubble which replaces a plug of liquid of equal length. In equation (5), if $\Delta(\Delta P)>0$, the insertion of a bubble increases the pressure drop, which leads to a risk of clogging the flow channel 3 with bubbles, whereas if $\Delta(\Delta P)<0$, the insertion of a bubble reduces the pressure drop and poses no risk to the continued flow through the channel.

Rearranging equation (5) we define a limiting bubble length $L_{bl}$, as $$L_{bl} = \frac{\partial \acute{a} D^3}{32 Q(\varsigma_1 - \varsigma_g)}. \quad (6)$$

Bubbles shorter than indicated by expression (6) lead to a risk of clogging the flow channel because the gain from lower viscosity of the gas is offset by the loss due to deformation; bubbles longer than indicated by expression (6) will flow freely along the flow channel because the gain from lower viscosity of the gas dominates.

Whether actual clogging will occur depends, of course, on the pressure margin which is available for driving the flow. Clogging will occur only if the total pressure differential between the source 12 and the recipient 13 is consumed by the sum of pressure drops from a train of bubbles and liquid plugs, according to equations (2) and (4).

As mentioned earlier, the occurrence of bubble fragmentation is unpredictable in flow restrictors of the simple configuration shown in FIG. 1. Investigation has shown, however, that the flow restrictor geometry may be modified to suppress the generation of bubbles below critical length. One example of such a modified geometry is shown in FIG. 2.

Figure 2:
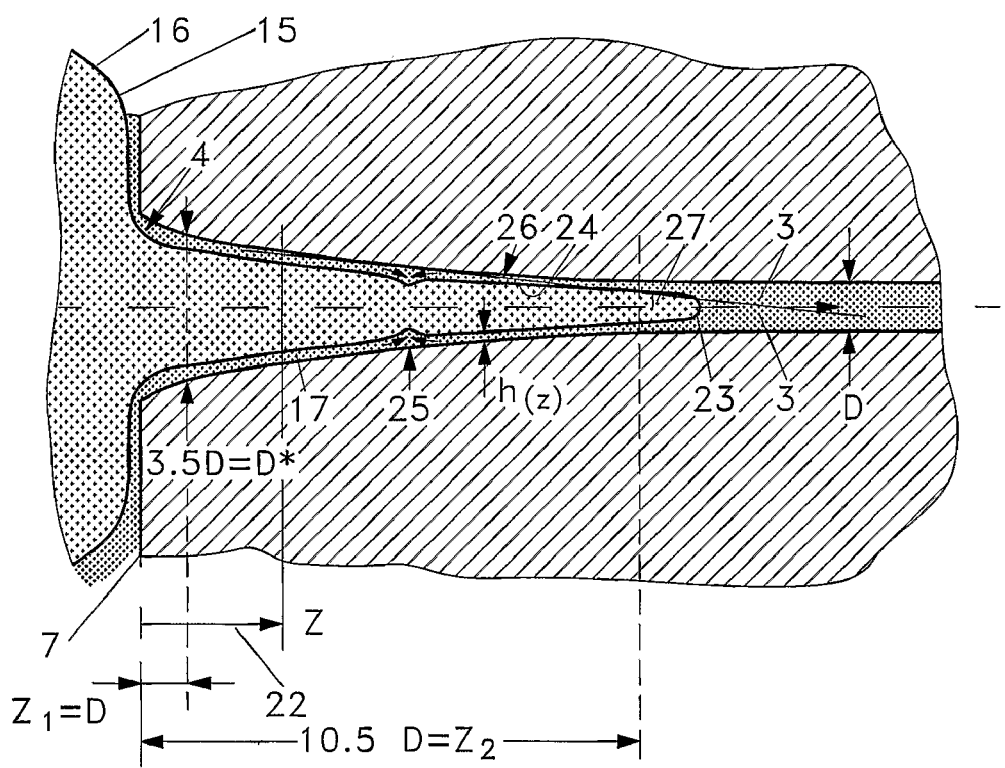

Shown in FIG. 2, on a larger scale than in FIG. 1, is the inlet end of a flow restrictor of a similar overall construction as in FIG. 1. There is a difference, however, in that the flow channel 3 has been smoothly and gradually widened at the inlet to form a trombone-shaped inlet mouth. Near the inlet face 7, the channel is wide. Further away from the inlet face the channel narrows down toward the original internal diameter D. In terms of the coordinate z set at zero at the inlet face 7 and pointing in the direction of flow as indicated at 22, at z=D the channel has an internal diameter D(z)=3.5D, and at z=10.5D the channel has an internal diameter D(z)=D.

A first rule for the widening of the channel 3 may be derived from the condition that the inlet geometry should at least allow the formation of bubbles long enough to avoid blocking of the channel 3. Letting N denote the number of bubbles present in the flow restrictor, flow will not be blocked if $$N \Delta P_d < \Delta P \tag{7}$$

wherein $\Delta P_d$ denotes the deformation pressure drop of each bubble as defined in (3) above. We now consider the pinch-off of a bubble in the widened part of the flow channel 3 at a point where the channel has an internal diameter D*>D. The volume of a bubble of length $L_{min} = \pi D^*$ at this point can be approximated as $$V_b = \partial D^* \frac{\partial}{4} D^{*2} = \frac{\partial^2}{4} D^{*3} \tag{8}$$

The maximum number N of such bubbles in a flow channel of length L is equal to the volume of the channel divided by the volume of a bubble:

$$N = \frac{\frac{\partial}{4} D^2 L}{\frac{\partial^2}{4} D^{*3}} = \frac{LD^2}{\partial D^{*3}} \tag{9}$$

By entering the expression (10) in expression (7) and combining with (2) and (3) above, we get $$\frac{LD^2}{\partial D^{*3}} \frac{4\acute{a}}{D} < \frac{128 Q \varsigma_1 L}{D^4} \tag{10}$$

which can be rearranged to give $$D^* > \sqrt[3]{\frac{\acute{a} D^5}{32 \varsigma Q}} \tag{11}$$

The physical interpretation of this expression is the following: If the inlet of the channel 3 is widened to a diameter slightly above D*, this at least creates the possibility that bubbles produced by fragmentation will be long enough to not completely stop the flow through the channel, even if the channel is filled up completely by such bubbles.

Turning now to our study of the fragmentation process itself, FIG. 2 shows a bubble 16 of gas 15 entering the channel 3. At the front 23 of the bubble, liquid is displaced by the gas to form a thin film 17 of thickness h(z) on the inner surface of the channel 3. Due the surface tension at the gas-to-liquid interface 24, the film 17 is unstable. The surface tension exerts a pumping action causing a tendency of the liquid to flow both radially and axially, as shown at 25, which is a well-known phenomenon in the field of hydrodynamics. This causes local accumulation of liquid which may eventually lead to the formation of a plug of liquid which fills the channel 3. Thus a smaller bubble 18 (not shown in FIG. 2) may be pinched off from the bubble 16.

Our investigations indicate that it is largely a matter of local surface curvature and timing whether pinch-off will actually occur or not. If the bubble 16 passes a site 25 of beginning local accumulation of liquid but the liquid film 17 does not reach sufficient thickness to form a liquid plug while the bubble passes, pinch-off will not happen. On the other hand, if the liquid film 17 grows thick enough to coalesce at the center of the channel 3 to form a liquid plug while the bubble 16 flows past the site 25, pinch-off will be the result.

Based on this it has now been found that by suitably widening the inlet of the flow channel dependent on the desired flow rate, it is possible to control the timing of perturbation growth of the liquid film around gas bubbles in the channel 3 in such a manner that any bubble fragmentation will lead to bubbles which are either longer than the limiting length of equation 6 and thus pose no risk of blocking the capillary, or short enough to reduce the flow but not numerous enough to stop the flow of liquid through the capillary.

From experimental and numerical studies it is known that a bubble moving along a straight capillary with the bubble velocity v(z) will be surrounded by a liquid film of thickness $$h(z) = \left( \frac{v(z) \varsigma_1}{\tilde{a}} \right)^{\frac{2}{3}} R(z) \tag{12}$$

wherein γ is the surface tension at the liquid-gas interface. As one would expect, a slowly moving bubble is surrounded by a thinner film of liquid than a fast-moving bubble. In case of standstill, a bubble will eventually displace all surrounding liquid and dry out the surface of the channel around it.

It may be said without making too much of an error that any bubble 18 moves with the same velocity as the surrounding liquid. Therefore $$v(z) = \frac{Q}{\partial R(z)^2} \tag{13}$$

wherein v(z) denotes the velocity of a bubble at the location z. For a bubble of length $L_b$ this leads to a bubble transit time $\tau_b$ at the location z of $$\delta_b(z) = L_b / v(z). \tag{14}$$

Bubble velocity has a characteristic (maximum) value v* at some coordinate z along the channel 3 where R(z) is at its minimum. Accordingly, bubble transit time has a characteristic (minimum) value $\tau_b$ with $$\delta_b = L_b / v^* \tag{15}$$

It is not only bubble velocity, however, which determines the film thickness. Since the liquid film adheres to the channel surface, it follows the surface closely. Film thickness can be influenced by controlling the shape of the channel surface.

As shown in FIG. 2 at 26, the channel surface at any coordinate z within the widened channel portion slopes inward with a slope defined as $$a(z) = -\frac{dR(z)}{dz} \tag{16}$$

and has a tangent at z with the corresponding tapering angle $$\grave{e}_T(z) = \arctan(a(z)) \tag{17}$$

relative to the longitudinal axis of the channel 3, as shown at 27 in FIG. 2. In a similar fashion as with the bubble velocity and transit time above, we define the maximum tapering angle in the capillary inlet as $\theta_T^*$.

It has been found that within the tapered channel portion, instabilities will typically cause a liquid film of thickness h(z) to coalesce at the center of the flow channel, and thereby to pinch off a bubble, within a local time period $\tau_p(z)$ of $$\hat{\sigma}_p(z) = \frac{0.01}{(\hat{e}_T^*)^{1.2}} \left(\frac{R(z)}{h(z)}\right)^3 \frac{3\varsigma_1 R(z)}{\tilde{a}}. \tag{18}$$

Our investigations indicate that the smallest of these local time periods, referred to as $\tau^*$, governs the time scale of bubble segmentation within the widened part of the channel 3.

As it is desired to prevent bubble fragmentation into bubbles shorter than the limiting bubble length given in equation (6), and the characteristic (minimum) transit time $\tau_{bl}$ of such bubbles is $$\delta_{bl} = L_{bl}/v^*, \tag{19}$$

a channel slope designed such that $$\hat{\sigma}^* > \hat{\sigma}_{bl} \tag{20}$$

will prevent the formation of bubbles having a length $L_b < L_{bl}$.

Relations (11) and (20) may then be combined in the design of the widened inlet to the channel 3 to form a flow restrictor which is tolerant to bubble fragmentation, as follows:

In a first section of the channel 3 between the inlet face 7 and a first z-coordinate $z_1$, the channel diameter D should be kept larger than the value D* given by relation (11) above. In this connection, the coordinate $z_1$ is defined as the first location along the channel where the channel diameter narrows down to D*. This will ensure that any bubble segmentation within the first section does not generate bubbles which are so short as to block the flow completely.

In a second section of the channel, between the z-coordinate $z_1$ and a second z-coordinate $z_2$, the channel should be designed to narrow down gradually towards the original channel diameter D in accordance with the relation (20) above. The second z-coordinate $z_2$ is defined as the first location along the channel where the channel narrows down to its original, overall diameter D. In practical terms this means that the geometry should be designed to minimize the change in surface curvature as the channel narrows down. This will ensure that bubbles which have reached $z_1$ unfragmented, or which have been fragmented at $z_1$ into bubbles of non-critical length, will not be further fragmented during their passage along the second channel section, and will enter into the remaining, straight section of channel 3 unfragmented and remain unfragmented also there.

We reserve the right to claim flow restrictors designed in accordance with relation (11), relation (20) or both, or any other relation disclosed in this patent application or any physical interpretation of any such relation. The embodiment shown in the drawings should be considered in a non-limiting fashion as being exemplary of a preferred way of practising the invention. As an alternative, flow restrictors of a similar nature may be made in planar technology by micromachining or embossing techniques, for example. In such realisations, it might be envisioned to connect several flow restrictors in series or parallel for specific purposes.

While the present invention has been illustrated and described with respect to a particular embodiment thereof, it should be appreciated by those of ordinary skill in the art that various modifications to this invention may be made without departing from the spirit and scope of the present invention.

What is claimed is:

1. A flow restrictor for restricting a flow of liquid, the restrictor comprising a body with an inlet face, an outlet face and a flow channel extending therebetween from an inlet to an outlet, the channel having over most of its length a diameter D, wherein the flow channel has been widened at least at the inlet in such a manner that at distances z from the inlet face:
   at z=D the channel has an internal diameter D(z)=3.5D, and
   at z≧10.5D the channel has an internal diameter D(z)=D, and in such a manner that internal diameter, D(z), is narrowed smoothly and gradually as a function of z.

2. The flow restrictor according to claim 1, wherein the geometry of the flow channel is designed to minimize the change in curvature in the widened part of the flow channel.

3. An apparatus for delivering a restricted flow of liquid to a recipient, the apparatus comprising a reservoir of liquid at higher pressure than the recipient, a flow restrictor as claimed in any preceding claim, a transfer conduit in fluid communication with the reservoir and the inlet of the restrictor, and a delivery conduit in fluid communication with the outlet of the restrictor and the recipient.

* * * * *